United States Patent
Leiner et al.

(10) Patent No.: US 8,343,042 B2
(45) Date of Patent: Jan. 1, 2013

(54) MAGNETICALLY ACTUATED ENDOSCOPE COUPLER

(75) Inventors: Dennis C. Leiner, Cape Elizabeth, ME (US); Michael Bush, South Portland, ME (US)

(73) Assignee: Lighthouse Imaging Corporation, Portland, ME (US)

( * ) Notice: Subject to any disclaimer, the term of this patent is extended or adjusted under 35 U.S.C. 154(b) by 1703 days.

(21) Appl. No.: 11/478,223

(22) Filed: Jun. 29, 2006

(65) Prior Publication Data

US 2007/0010707 A1 Jan. 11, 2007

Related U.S. Application Data

(60) Provisional application No. 60/698,256, filed on Jul. 11, 2005.

(51) Int. Cl.
*A61B 1/06* (2006.01)

(52) U.S. Cl. .......................... 600/167; 600/173

(58) Field of Classification Search .................. 600/121, 600/163, 174, 162, 112; 310/103, 104, 80, 310/43, 12.14; 359/701, 823, 819, 822; 396/85, 396/89, 131, 133, 144, 25–29.17; 348/45, 348/65

See application file for complete search history.

(56) References Cited

U.S. PATENT DOCUMENTS

| | | | |
|---|---|---|---|
| 3,765,748 A * | 10/1973 | Mito | 359/701 |
| 4,315,670 A * | 2/1982 | Shigoku | 359/701 |
| 5,056,902 A | 10/1991 | Chinnock et al. | |
| 5,145,614 A * | 9/1992 | Kuroda | 264/429 |
| 5,359,992 A | 11/1994 | Hori et al. | |
| 5,694,621 A * | 12/1997 | Dowe et al. | 396/25 |
| 5,706,143 A | 1/1998 | Hipp | |
| 5,836,867 A * | 11/1998 | Speier et al. | 600/112 |
| 5,952,744 A * | 9/1999 | Chitayat | 310/12.31 |
| 5,978,161 A * | 11/1999 | Lemke | 359/824 |
| 6,099,467 A | 8/2000 | Kehr et al. | |
| 6,522,477 B2 | 2/2003 | Anhalt | |
| 6,616,602 B1 | 9/2003 | Witte | |
| 6,632,173 B1 | 10/2003 | Kehr et al. | |
| 6,633,438 B2 | 10/2003 | Anhalt | |
| 2001/0043016 A1* | 11/2001 | Chun et al. | 310/12 |
| 2002/0084880 A1* | 7/2002 | Barbera-Guilem et al. | 336/200 |
| 2003/0103279 A1* | 6/2003 | Anhalt | 359/826 |
| 2004/0099346 A1* | 5/2004 | Nishiuchi et al. | 148/302 |
| 2006/0023320 A1* | 2/2006 | Kimura et al. | 359/689 |

FOREIGN PATENT DOCUMENTS

WO  WO 2004040350 A1 *  5/2004

* cited by examiner

*Primary Examiner* — Matthew J Kasztejna
*Assistant Examiner* — Alexandra Newton
(74) *Attorney, Agent, or Firm* — Pierce Atwood LLP

(57) ABSTRACT

An endoscopic coupler by which the rotary and/or linear motion of an external ring is transferred via magnetic interaction of specially configured continuous plastic magnets to a lens resident in a hermetically sealed housing to effect focusing and/or zooming action of the lens without mechanically breaching the integrity of the hermetic seal thereby making the coupler particularly suitable for withstanding the rigors of autoclaving.

6 Claims, 4 Drawing Sheets

MAGNETICALLY ACTUATED ENDOSCOPE COUPLER

CROSS-REFERENCE TO RELATED APPLICATION

This application claims the benefit of priority from U.S. Provisional Patent Application No. 60/698,256 entitled MAGNETICALLY ACTUATED ENDOSCOPE COUPLER and filed on Jul. 11, 2005 in the name of Dennis C. Leiner, et al., the entire contents of which are incorporated herein by reference.

BACKGROUND OF THE INVENTION

This invention generally relates to the field of endoscopic systems adapted to permit the visualization of otherwise visually inaccessible objects, such as interior body cavities, organs and tissue, and the like. More particularly, the invention relates to magnetically actuated endoscope couplers for use in connecting video cameras and the like to the proximal end of an endoscope to display and record endoscopic images while performing surgical procedures or performing exploratory operations for diagnostic purposes.

Endoscopic couplers are well known in the endoscopic art, and typically comprise a sealed housing in which a lens resides to relay the image formed at the proximal end of the endoscope to one or more cameras. Provision is made at both ends of the coupler for connecting the endoscope eyepiece to one end and the camera to the other. Like all artifacts used in invasive surgical procedures, endoscope couplers need to be kept sterile to prevent infection through the transfer and spread of bacteria. To assure this, autoclaving procedures are used to sterilize couplers with pressurized steam. Because the autoclave environment is inherently hostile, it is important for the couplers to be robustly hermetically sealed; otherwise, their integrity will be compromised and infection will be possible.

One approach that has been used to provide couplers with focusing capability while maintaining hermetically sealed has been to magnetically couple the mechanical rotary motion of an external focusing ring to linear motion of one or more of the elements of the coupler lens, which resides in a hermetically sealed housing. However, the various magnetic coupling arrangements of the art, which use discrete magnets, can become unsynchronized when the original alignment of their magnets with their intended axial focus position gets disrupted with jarring or the like.

Consequently, it is a primary purpose of the invention to construct an endoscopic coupler (suitable for, but not limited to, autoclaving) where the optical elements are held within a sealed volume.

Another object of the invention is to overcome a common failure mode for endoscopic couplers where moisture migrates thru dynamic seals by a novel magnetic coupler that addresses this problem by eliminating the dynamic seals.

Other objects of this invention will, in part, be obvious, and will, in part, appear hereinafter when the following detailed description is read in connection with the accompanying drawings.

SUMMARY OF THE INVENTION

The invention relates to using low cost, low magnetic energy plastic magnets instead of the rare-earth magnets for effecting focusing and zooming action of hermetically sealed endoscopic lens.

According to an aspect of the invention, an endoscopic coupler for relaying an image formed at the distal end of an endoscope to a detector located downstream of the coupler is provided where the coupler comprises a hermetically sealed housing having transparent entrance and exit windows. Also included is a lens cell slidably mounted for translation in the hermetically sealed housing. A lens is mounted within the lens cell for receiving light through the entrance window and imaging it through the exit window and onto the detector. A focusing ring is mounted outside of the hermetically sealed housing for relative rotation with respect thereto. A mechanical arrangement is provided within the hermetically sealed housing and is adapted to translate the lens cell to move the lens along its axis. A first continuous plastic multi-pole magnet fixedly is mounted to the focusing ring for movement therewith as it is rotated, and a second continuous plastic multi-pole magnet mounted inside of said hermetically sealed housing for relative rotation with respect thereto, said second continuous plastic multi-pole magnet being configured and arranged to rotate as said focusing ring is rotated and being coupled to said mechanical arrangement so that the rotary motion thereof causes said lens cell to translate along the axis of said lens to focus it.

The use of plastic magnets offers a number of advantages over the prior art:
(1) significantly reduced costs;
(2) due to more distributed, and thus lower magnetic energy, reduced likelihood of interfering with external devices, or of attracting Ferro-magnetic debris;
(3) plastic magnets lend themselves to custom spacing of the magnetic poles. This permits the construction of "quilt pattern" magnets as shown in the attached drawing;
(4) plastic magnets can be fabricated into thinner sections than most other types of magnets. This is significant because it allows the construction of a smaller coupler; and
(5) plastic magnets can be fabricated with relatively arbitrary numbers of poles per inch, permitting customization of the turning torque. This property is also useful because, in the arrangement shown in FIG. 3, the outer magnet has fewer poles per inch than the concentric inner magnet.

BRIEF DESCRIPTION OF THE DRAWINGS

The structure, operation, and methodology of the invention, together with other objects and advantages thereof, may best be understood by reading the detailed description in connection with the drawings in which each part has an assigned numeral or label that identifies it wherever it appears in the various drawings and wherein:

FIG. 4b is a developed plan view of one of the magnets of FIG. 4a;

DETAILED DESCRIPTION

Figure 1:
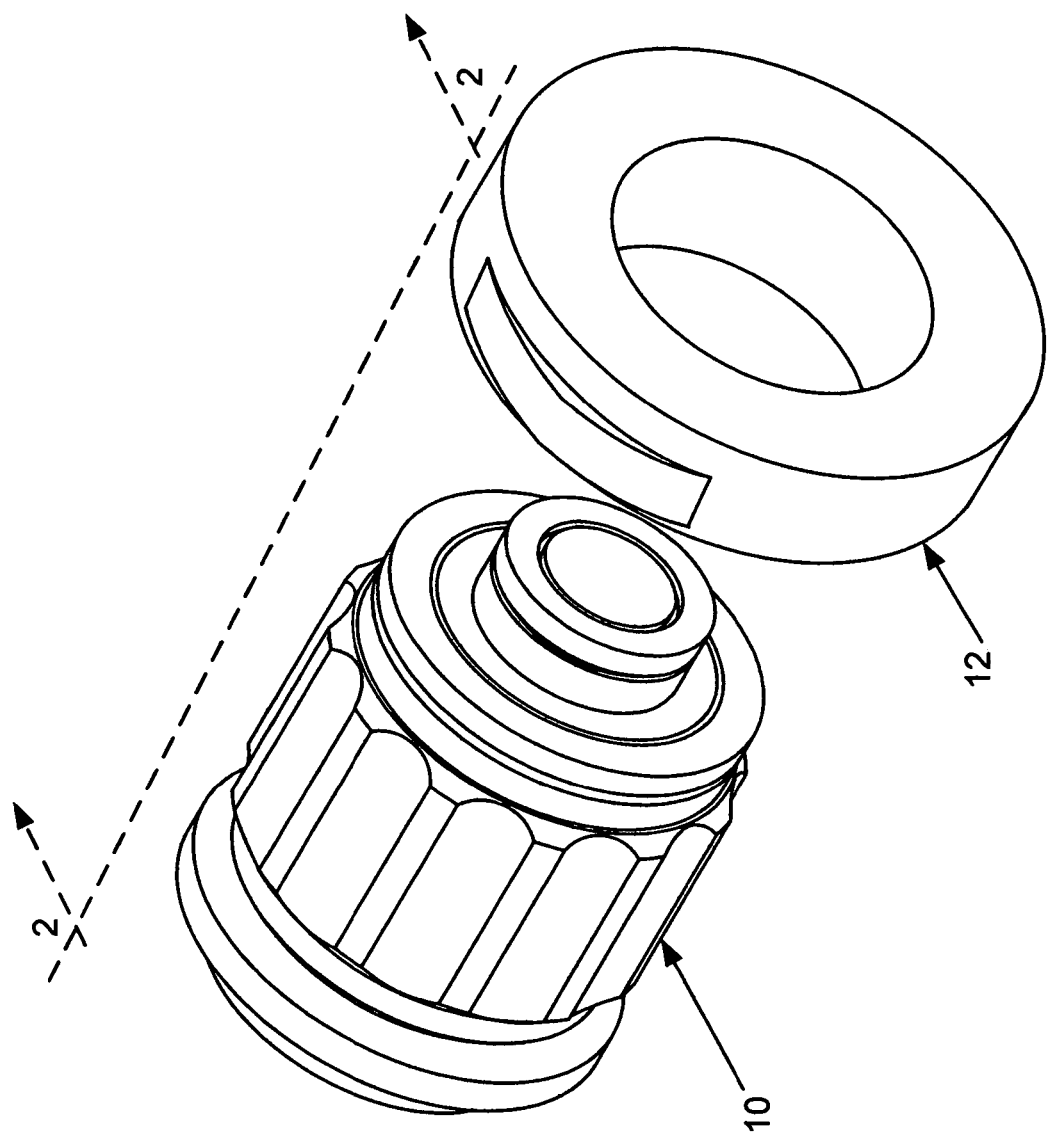
FIG. 1 is a diagrammatic perspective view of a magnetically actuated endoscope coupler shown in combination with endoscope mount.

Reference is now made to FIG. 1 which shows an embodiment of a magnetically actuated endoscopic coupler 10 of the invention ("coupler") in combination with an endoscope mount 12 that is used in a well-known manner to mechanically attach an endoscope's eyepiece with one end of the coupler 10 so that the image formed near (downstream) the proximal end of the endoscope can be relayed to a detector for subsequent electronic processing and display. The coupler 10 also may scale the image with this operation.

Figure 2:
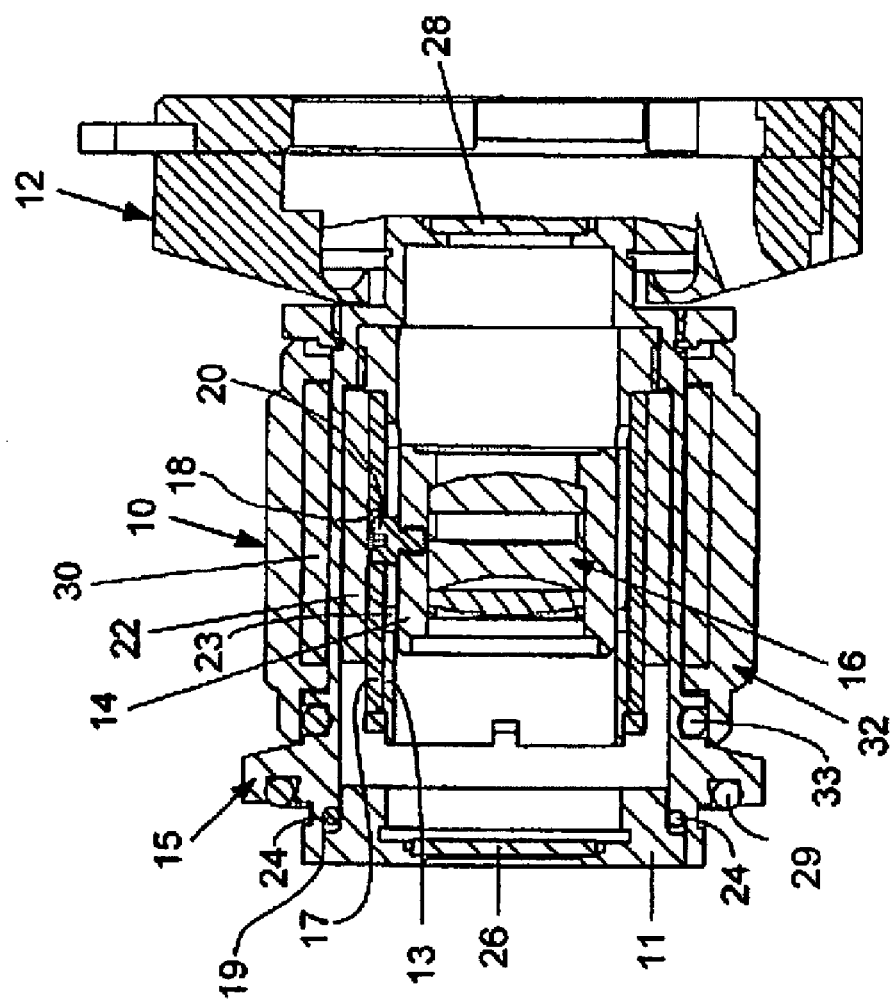
FIG. 2 is a diagrammatic cross-sectional side view of the magnetically actuated endoscope coupler of FIG. 1 taken along line 2-2 in that figure.

Reference is now made to FIG. 2 which shows a diagrammatic cross-section view of the coupler 10 and endoscope mount 12 taken generally along lines 2-2 in FIG. 1, except with the coupler 10 and endoscope mount engaged. As best seen in the cross-sectional view of the coupler 10 shown in FIG. 2, a lens cell 14 carries a three-element lens 16, and the lens cell 14 slides in a sleeve 13 provided with an elongated slot 23. The lens cell 14 otherwise resides in an outer main housing 15 and is mounted for longitudinal motion along its axis to adjust focus. The lens cell 14 is moved longitudinally via a drive pin 20 with one end fixed to the lens cell 14. The head of the drive pin 20 extends through the elongated slot 23 in the sleeve 13 and slides in a helical groove 18 formed in a cylindrical tube 17 or inner ring. As mentioned, the drive pin 20 is fixed to the lens cell 14, and the cylindrical tube 17 with the helical groove 18 is fixed to an inner, virtually continuous, plastic inner annular magnet 22 that is bonded to the cylindrical tube 17 to move in concert with it. The plastic inner annular magnet 22 is preferably molded into a cylindrical tube or, alternatively, formed of a magnetic strip and attached to the outer surface of the cylindrical tube 17, surrounding the lens cell 14.

The three element lens 16 is hermetically sealed in the main housing 15 with a suitable sealing arrangement, and light enters and exits the lens 16 via sapphire windows 26 and 28 provided at either end of the main housing 15. Saffire window 26 is carried on a mount 11 which is preferably hermetically sealed to main housing 15 by laser welding the two together at the seam 19 formed where they interface. The hermetic seal may also be achieved through the use of an O-ring 24 located behind where the laser weld 19 is preferably made. The ends of the main housing 15 are also adapted for mechanical attachment to the endoscope mount 12 and a standard camera "C"-mount, the front end being provided with a camera O-ring 29 for this purpose. Another O-ring 33 is provided to control the "feel" of the focusing ring 32 by selectively controlling the torque required to move it.

An outer magnet 30, similar in properties to the inner magnet 22, is bonded to a focus ring 32, and its magnetic field interacts with that of the inner magnet 22 so that rotary motion of the focus ring 32 causes rotary motion of the inner magnet 22. As shown, the pair of substantially cylindrical magnets 22 and 30 is used to transfer force from the free-spinning focus ring 32 across a sealed housing to a helix drive arrangement.

As the cylindrical tube 17 turns, it causes axial movement of the co-axial lens cell since the drive pin 20 turns and slides in helical groove 18.

The magnets 22 and 30 can be fabricated as cylindrical components, and bonded to the other components as needed. Alternatively, the magnets 22 and 30 may be fabricated from flat flexible magnet stock (commonly used for refrigerator magnets or from Plastiform® magnet material) and glued to the cylindrical metal parts. Plastiform® magnet materials, which are particularly suitable for the present application, are marketed by Arnold, The Magnetic Products Group of SPS Technologies, Rochester, N.Y. These magnetic materials are made by combining high quality thermoset resins with magnetic powders (rare earths and barium ferrite) and compression molding the mix into dimensionally precise die cavities. The magnets offer an excellent combination of strong magnetics and dimensional stability with good strength, resistance to breakage, and corrosion resistance. Performance at higher temperature or in corrosive environments may be improved through the use of protective coatings.

Figure 3:
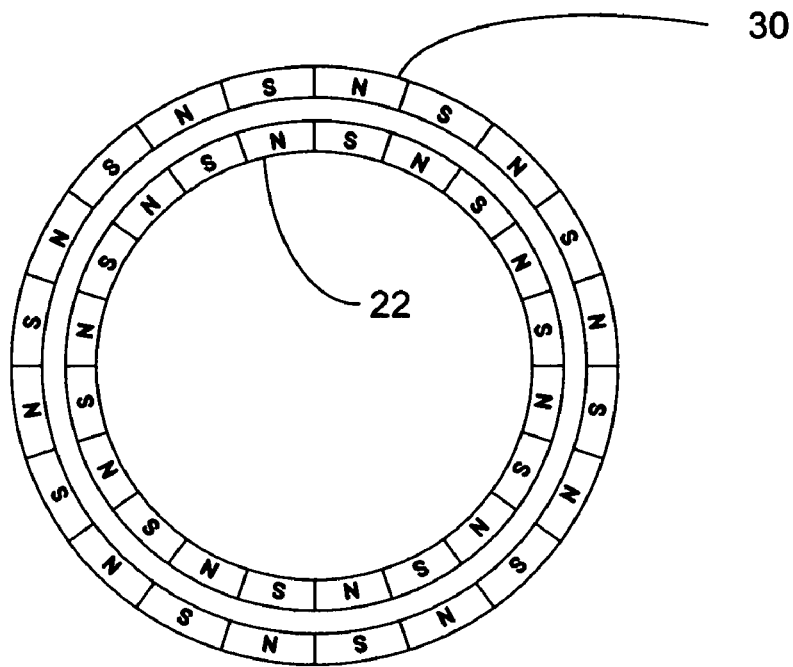
FIG. 3 is a diagrammatic representation of the virtually continuous magnetic pole arrangement of the plastic magnetic strips used in the coupler of the invention to effect focusing action.

Both methods are commonly used for the fabrication of permanent magnet motor stators and in brushless motor rotors. FIG. 3 shows the magnetic pole arrangement for achieving focusing while still maintaining a hermetic seat.

Regardless of fabrication method, the magnets are arranged with a non-magnetic metal wall (nominally ~0.035 inches thick) separating them. Prototypes of this arrangement have been found to transfer sufficient force for endoscopic coupler applications.

An additional advantage of the invention is that the numerous pairs of magnetic poles do not have any required orientation. This has the following advantages:

(1) In the event that the coupler 10 is dropped and the lens cell 14 shifts, the link between the two magnets 22 and 30 is not lost. The magnetic pairings may shift by one or more increments, but the continuous nature of the multi-polar magnetic arrangement prevents the magnetic circuit from failing; and (2) Magnetic couplers in the prior art have had to employ stops to prevent the focus ring from turning too far. If the lens cell was to come up against a hard stop, and the user was to keep turning, the magnetic coupling could be lost. In some prior art designs, it is difficult or impossible to restore the magnetic coupling once it is lost. In the invention, if the lens cell 14 comes up against a hard stop and the user keeps turning, the magnets "cog" over to the next pair of magnetic poles, but the coupling is not lost. This effect has been demonstrated during modeling. In the focusing application, it will be understood that, in the magnetic arrangement of FIG. 3, the inner magnet 22 follows the rotation of the outer magnet 30. A further advantage of this arrangement is that an asymmetrical focus ring may be employed, allowing an optimal ergonomic shape for both right handed and left handed users or a single focusing tab may be provided and selectively cogged into positions appropriate for left or right handedness.

Commercially available photographic zoom lenses utilize a dual-purpose focus ring where rotation of a ring changes the focus while axial movement of the ring changes the focal length ("zooms") the unit. One known dual-purpose zoom adaptor is marketed by Lighthouse Imaging Corporation, Portland, Me. The Lighthouse Imaging zoom endoscope adaptor provides a lightweight means of attaching endoscope eyepieces to standard c-mount video cameras and a unique ergonomic method for changing image magnification. While most zoom endoscope adaptors utilize a confusing set of two knobs to separately adjust zoom and focus, the Lighthouse zoom adaptor uses a single knob which quickly and easily performs both tasks, freeing the surgeon to maintain focus on the surgery during camera adjustment. Custom designed and manufactured optics are employed to provide sharp images across the entire field of view. An embodiment of the present zoom coupler uses the same principal for an endoscopic zoom coupler, but differently implemented.

Figure 4B:
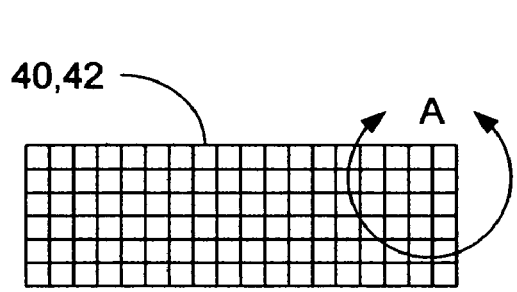
Figure 4A:
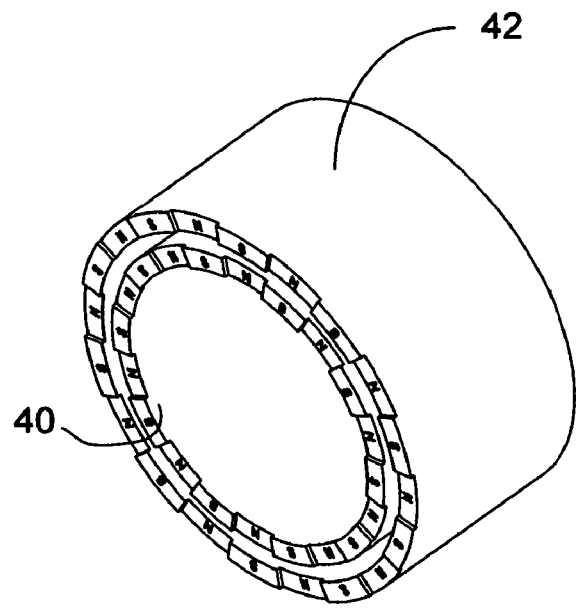
FIG. 4a is a diagrammatic perspective view of a pair of concentric magnets having a predetermined "quilt" magnetic pole arrangement to be used to effect both focusing and zooming action with a modified version of the invention shown in FIGS. 1 and 2.
Figure 4C:
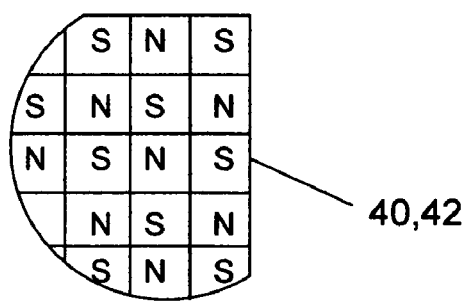
FIG. 4c is an enlarged fragment of the magnet of FIG. 4b enclosed within circle "A" showing its magnetic quilt arrangement.

Reference is now made to FIGS. 4a, 4b, and 4c, which illustrate an inner and outer magnet arrangement that uses magnets with quilt pattern to achieve both focusing and zooming in one simple action. As seen in FIG. 4a, this arrangement comprises an inner magnetic ring 40 and an outer magnetic ring 42. FIG. 4b shows a diagrammatic developed plan view of a checkered pattern in which the magnetic elements of magnets 40 and 42 are arranged in "quilted" fashion, with alternating poles arranged in a regular matrix as shown in FIG. 3c. Using a quilt pattern magnet as shown in either the Lighthouse Imaging Zoom adapter or a modified version of the embodiment of FIGS. 1 and 2, permits the outer focusing ring to axially, as well as rotationally move, thus allowing for both rotary and axial actuation, and thereby permits the development of a single knob magnetic zoom coupler. As can be appreciated from the detail of FIG. 4c, axial movement of the quilted pattern would cause the lens cell 14 to move along the axis to change focal length, "zoom", while rotary motion controls focusing. That is, rotation of the outer ring 32 imposes a torque on the inner ring (cylindrical tube 17) causing it to rotate, and axial movement of the outer ring 32 generates an axial push or pull force on the inner ring causing it to translate along the optical axis of the lens. Again, the multi-pole arrangement is readily fabricated by exposing the plastic bonded magnetic materials to the appropriate magnetizing field to cause proper alignment of the magnetic material incorporated in the plastic matrix. To effect the necessary axial motion for zooming, i.e., magnification change, one of the lens elements of, for example, the lens of FIG. 2 is arranged to move axially with respect to the others in the lens cell 14 while the slot sleeve 13, which carries the lens cell is caused to move axially with translation of the focusing ring 32. This is achieved by providing a linear slot from the focusing ring through all intervening structure directly to the lens element to be moved relative to the others while also permitting for translation as well as rotation of the focusing ring as before.

Modern endoscope systems have begun to use HD (high definition) imaging to achieve a sharper image for the physician. In order to achieve true HD quality, the camera, endoscope, and coupler all have to be designed for HD image resolution. This presents large challenges to the lens designer regarding the coupler lens design. In addition, it is often the case that the camera sensor utilized with HD video systems is of the smaller ¼-inch format. In order to use this format with a standard C-mount thread, the back focal length of the coupler lens needs to be longer than the required effective focal length. Such a system is known as a reverse telephoto lens.

In addition, in order to make an endoscope coupler autoclavable, all materials used must be compatible with the high temperatures utilized in the autoclaving process. While clear adhesives exist that can withstand autoclave temperatures, these may be impractical to use because they may conflict with the standard manufacturing processes employed by some lens manufacturers. It is therefore desirable to eliminate all bonded lenses in the optical design.

Figure 5:
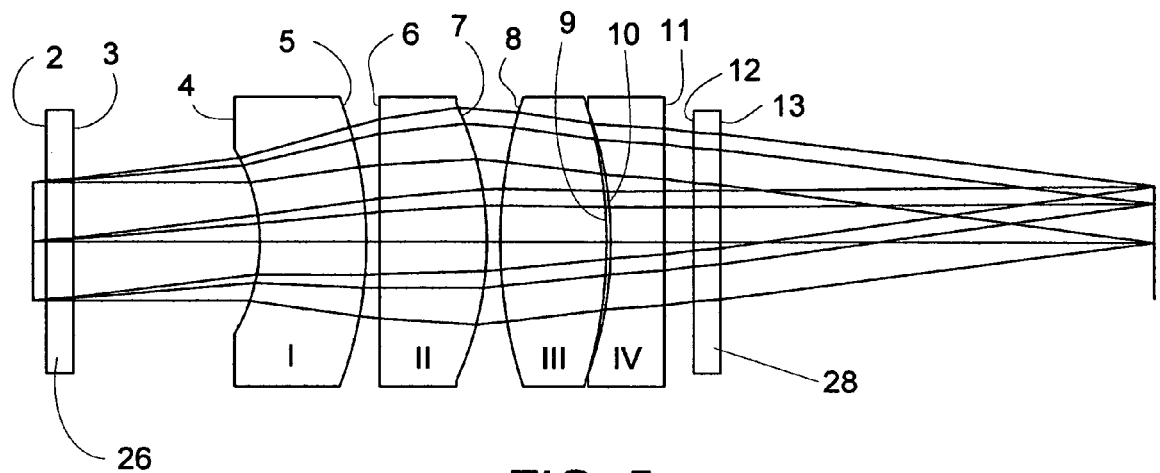
FIG. 5 is a diagrammatic elevational view of an alternate lens design that may be used in the magnetically actuated endoscopic coupler of the invention to provide HD imaging.

All of the above requirements have been combined into one lens design. In other words a lens system that has the following specifications:
(1) Has an image sharpness compatible with HD cameras;
(2) Eliminates lens adhesives; and
(3) Has a short effective focal length compared with its back focal length The layout of the referenced lens design is shown in FIG. 5 and its corresponding constructional data is as follows:

System Prescription Data

Entrance Pupil Diameter=4.5
Effective Focal Length: 16.99781
Back Focal Length: 16.25383
F/#: 3.771213
Paraxial Image Height: 2.162394
Maximum Radial Field: 7.25
Primary Wavelength: 0.55 μm
Lens Units: Millimeters
Surface Data Summary:

| Surf | Radius | Thickness | Glass |
|---|---|---|---|
| OBJ | Infinity | Infinity | |
| STO | Infinity | 0.5 | |
| 2 | Infinity | 1 | SAPPHIRE |
| 3 | Infinity | 6.998398 | |
| 4 | −6.95 | 4 | H-ZF4 |
| 5 | −15.47 | 0.5 | |
| 6 | Infinity | 4 | H-ZLAF50B |
| 7 | −12.8 | 0.5 | |
| 8 | 18.17 | 4 | H-ZK14 |
| 9 | −18.17 | 0.16 | |
| 10 | −14.92 | 2 | H-ZF52 |
| 11 | Infinity | 1.091602 | |
| 12 | Infinity | 1 | SAPPHIRE |
| 13 | Infinity | 16.25 | |
| IMA | Infinity | | |

As will be appreciated, the lens described with the foregoing constructional data and as shown in FIG. 5 may be used in the coupler of FIGS. 1 and 2, and their variants, but with slight modification to the mechanical configuration of the coupler.

Figure 6:
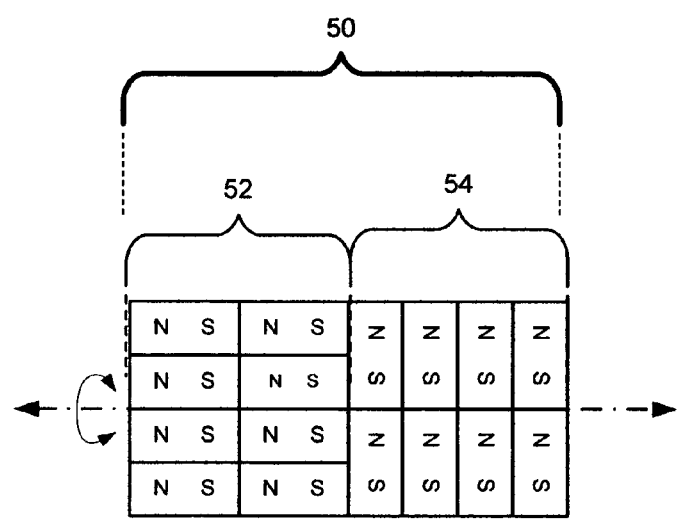
FIG. 6 is a diagrammatic elevational view of an alternate magnetic arrangement for effecting focusing and zooming action in which the magnetic action for both is separated rather than quilted.

A variant of the "quilted" magnetic ring arrangement of FIGS. 4a through 4c is illustrated in FIG. 6 where it is designated at 50. As shown there, the function of the "quilt" arrangement previously described is broken into two separate magnetic ring segments, a translation segment 52 and a Rotation segment 54. This segmented arrangement operates in a fashion similar to the operation of the "quilted" rings, and may afford manufacturing benefits compared with the "quilted" embodiment.

Other variants of the invention will be apparent based on its teachings, and all such variants are considered to be within the scope of the invention.

What is claimed is:
1. An endoscopic coupler for relaying an image formed at the distal end of an endoscope to a detector located downstream of the coupler, said coupler comprising:
 a hermetically sealed housing having transparent entrance and exit windows arranged along an optical axis;
 a lens cell slidably mounted for translation in said hermetically sealed housing along said optical axis;
 a lens mounted within said lens cell for receiving light through said entrance window and imaging it through said exit window and onto the detector;

a focusing ring mounted outside of said hermetically sealed housing for relative rotation with respect thereto;

a mechanical arrangement located within said hermetically sealed housing and adapted to translate said lens cell to move said lens along its axis;

a first continuous plastic cylindrical tubular magnet fixedly mounted to said focusing ring for movement therewith as said focusing ring is rotated, said first continuous plastic cylindrical tubular magnet comprising a plastic binder having magnetic powder distributed throughout and aligned as continuous magnetic poles that alter in polarity around the circumference of said first continuous plastic cylindrical tubular magnet but do not alter in polarity along its axial length; and a second continuous plastic cylindrical tubular magnet mounted inside of said hermetically sealed housing for relative rotation with respect thereto, said second continuous plastic cylindrical tubular magnet also comprising a plastic binder having magnetic powder distributed throughout and aligned as continuous magnetic poles that alter in polarity around the circumference said second continuous plastic cylindrical tubular magnet but do not alter in polarity along its axial length, said second continuous plastic cylindrical tubular magnet being configured and arranged to rotate as said focusing ring is rotated and being coupled to said mechanical arrangement so that the rotary motion thereof causes said lens cell to translate along the axis of said lens to focus it.

2. The endoscopic coupler of claim 1 wherein both said first and second continuous plastic cylindrical tubular magnets have a magnetic pole arrangement such that relative rotation of one with respect to the other causes the other to rotate and relative translation of one with respect to the other causes the other to translate so that both focusing and zooming action may be effected.

3. The endoscopic coupler of claim 1 comprising at least two pairs of continuous plastic cylindrical tubular magnets such that relative rotation of one magnet of the first pair with respect to the other magnet of the first pair causes the other to rotate and move at least one element of said lens to effect focusing action and relative rotation of the second pair with respect to the other magnet of the second pair causes the other to rotate and move at least one other element of said lens to effect zooming action.

4. The endoscopic coupler of claim 1 wherein said lens comprises a reversed telephoto lens.

5. The endoscopic coupler of claim 4 wherein said reversed telephoto lens is configured to form high definition (HD) images on said detector.

6. The endoscopic coupler of claim 1 wherein said continuous plastic cylindrical tubular magnets are molded as thin walled hollow cylinders having an axial length substantially greater than their thickness.

* * * * *